United States Patent
Popovic et al.

(10) Patent No.: US 11,284,777 B2
(45) Date of Patent: Mar. 29, 2022

(54) ROBOTIC CONTROL OF AN ENDOSCOPE FROM ANATOMICAL FEATURES

(71) Applicant: KONINKLIJKE PHILIPS N.V., Eindhoven (NL)

(72) Inventors: Aleksandra Popovic, Boston, MA (US); Haytham Elhawary, New York, NY (US); Michael Chun-Chieh Lee, Lexington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 489 days.

(21) Appl. No.: 14/889,897

(22) PCT Filed: Apr. 30, 2014

(86) PCT No.: PCT/IB2014/061100
§ 371 (c)(1),
(2) Date: Nov. 9, 2015

(87) PCT Pub. No.: WO2014/181222
PCT Pub. Date: Nov. 13, 2014

(65) Prior Publication Data
US 2016/0066768 A1    Mar. 10, 2016

Related U.S. Application Data

(60) Provisional application No. 61/821,363, filed on May 9, 2013.

(51) Int. Cl.
*A61B 1/00* (2006.01)
*A61B 34/30* (2016.01)
*A61B 90/00* (2016.01)

(52) U.S. Cl.
CPC ........ *A61B 1/00006* (2013.01); *A61B 1/0005* (2013.01); *A61B 1/00009* (2013.01);
(Continued)

(58) Field of Classification Search
CPC .............. A61B 34/20; A61B 2034/105; A61B 2034/107; A61B 5/065; A61B 34/25;
(Continued)

(56) References Cited

U.S. PATENT DOCUMENTS

2003/0000535 A1   1/2003  Galloway
2004/0059217 A1   3/2004  Kessman
(Continued)

FOREIGN PATENT DOCUMENTS

DE   102011082444 A1   12/2012
EP        2277441 A1    1/2011
(Continued)

*Primary Examiner* — Alexandra L Newton (57) ABSTRACT

A robotic control system employs a robot unit (10) and a control unit (20). The robot unit (10) includes an endoscope (12) for generating an endoscope image (14), and a robot (11) for moving the endoscope (12) within an anatomical region. The control unit (20) includes an endoscope controller (22) for a determination of an endoscope pose within the anatomical region for an intraoperative visualization of the anatomical feature within the endoscope image (14), wherein the endoscope path is derived from a delineation of a volume coordinate position of the anatomical feature within a pre-operative image (43) of the anatomical region. The control unit (20) further includes a robot controller (21) for commanding the robot (11) to move the endoscope (12) to the endoscope pose within the anatomical region to visualize the anatomical feature within the endoscope image (14).

23 Claims, 6 Drawing Sheets

(52) U.S. Cl.
CPC .......... *A61B 1/00149* (2013.01); *A61B 34/30* (2016.02); *A61B 1/0016* (2013.01); *A61B 2034/301* (2016.02); *A61B 2090/365* (2016.02); *A61B 2090/373* (2016.02)

(58) Field of Classification Search
CPC ...... A61B 2090/365; A61B 2034/2055; A61B 34/10; A61B 2090/367; A61B 2090/364; A61B 1/00149; A61B 1/00156
USPC .......................................... 600/114, 117, 118
See application file for complete search history.

(56) References Cited

U.S. PATENT DOCUMENTS

| | | | |
|---|---|---|---|
| 2006/0271056 A1* | 11/2006 | Terrill-Grisoni ... | A61B 17/1703 606/84 |
| 2008/0010706 A1 | 1/2008 | Moses et al. | |
| 2008/0081982 A1* | 4/2008 | Simon ................. | A61N 5/1048 600/407 |
| 2008/0123927 A1 | 5/2008 | Miga et al. | |
| 2010/0249507 A1* | 9/2010 | Prisco ................ | A61B 1/00009 600/117 |
| 2012/0053408 A1* | 3/2012 | Miyamoto ........... | G06T 7/0044 600/109 |
| 2012/0249507 A1* | 10/2012 | Chung ................ | G09G 3/3614 345/211 |
| 2013/0165948 A1 | 6/2013 | Popovic | |
| 2013/0245375 A1 | 9/2013 | Dimaio et al. | |

FOREIGN PATENT DOCUMENTS

| | | | | |
|---|---|---|---|---|
| RS | WO 2012035492 A1 * | 3/2012 | ........... | A61B 1/0005 |
| WO | 2012035492 A1 | 3/2012 | | |
| WO | 2012065058 A2 | 5/2012 | | |
| WO | 2012071571 A2 | 5/2012 | | |
| WO | 2013061225 A1 | 5/2013 | | |

* cited by examiner

ROBOTIC CONTROL OF AN ENDOSCOPE FROM ANATOMICAL FEATURES

CROSS-REFERENCE TO PRIOR APPLICATIONS

This application is the U.S. National Phase application under 35 U.S.C. §371 of International Application No. PCT/IB2014/061100, filed on Apr. 20, 2014, which claims the benefit of U.S. Provisional Patent Application No. 61/821,363, filed on May 9, 2013. These applications are hereby incorporated by reference herein.

The present invention generally relates to robotic control of an endoscope during a minimally invasive surgery (e.g., a minimally invasive coronary bypass grafting surgery). The present invention specifically relates to the robotic control being based upon a determination of an endoscope pose within the anatomical region for visualizing an anatomical feature within an endoscope image.

Minimally invasive surgery is performed using elongated instruments inserted into a patient's body through small ports. For a surgery involving an endoscope, an endoscopic camera is inserted into a port to provide visualization of the surgical site. For example, a surgeon may hold and manually control two (2) laparoscopic instruments during the surgery while a physician assistant controls the endoscope and receives instructions from the surgeon to move the endoscope to specific locations during the surgery.

The surgeon's communication to the physician assistant of an exact desired location of the endoscope may be difficult, especially given the challenging hand-eye coordination required to move the endoscope and instruments around the pivot points at the entrance ports to the body, and given the different positions and frames of reference of the surgeon, physician assistant and a video image of the surgical site. For example, "Left" on the video image, may mean "right and down" at the physician assistant's hands. To overcome these difficulties, controlling the endoscope using an automated device or robot has been proposed in prior art, essentially removing the physician assistant from this task during surgery. However, given that the surgeon is controlling two (2) laparoscopic instruments with both hands, the method with which the physician can control the robotic endoscope is important, and a number of propositions have been addressed in prior art.

Generally, the prior art methods for guiding a robotic system are premised on (1) guiding the robot using different input devices (e.g., head motion sensors, a joystick or voice control), (2) guiding the robot using live endoscope images by determining a three-dimensional position of an anatomical feature with respect to the endoscope and moving the endoscope or a surgical instrument toward that anatomical feature, or (3) guiding the robot from other types of images using live image and recorded intra-operative images.

More particularly, human-robot interaction methods known in art use either specialized hardware or live and/or recorded intra-operative images to move the robot to a desired location. These methods assume that the user knows location of the anatomical feature of interest with respect to the endoscope and that the particular anatomical feature is visible in the endoscope view. This is not always true, as the anatomical feature may be obstructed within the endoscope view (e.g., coronary arteries may be covered with fat) or may be outside of the endoscope view.

The present invention provides methods for delineating a volume coordinate position of an anatomical feature within a pre-operative image of the anatomical region to facilitate an intra-operative visualization of the anatomical feature within an endoscope image of the anatomical region, particularly for an anatomical feature partially or entirely invisible in the endoscope image (e.g., obstructed within endoscope view or outside of endoscope view).

The term "visualize" or any variation thereof as used herein is broadly defined to describe a robotic control of an endoscope within an anatomical region whereby an anatomical feature of interest or section(s) therefore are either visible, partially or entirely, within the endoscope image or obstructed from being visible within the endoscope image yet susceptible to a surgeon forming a mental picture of an outline of the anatomical feature or section(s) thereof, partially or entirely, within the endoscope image.

One form of the present invention is a robotic control system employing a robot unit and a control unit. The robot unit includes an endoscope for generating an endoscope image, and a robot for moving the endoscope within an anatomical region. The control unit includes an endoscope controller to determine an endoscope pose within the anatomical region for an intra-operative visualization of an anatomical feature within the endoscope image, wherein the endoscope pose is derived from a delineation of a volume coordinate position of the anatomical feature within a pre-operative image of the anatomical region. The control unit further includes a robot controller to command the robot to move the endoscope to the endoscope pose within the anatomical region to visualize the anatomical feature within the endoscope image.

A second form of the present invention is a robotic control method for an endoscope for generating an endoscope image and a robot for moving the endoscope within the anatomical region. The robotic control method involves a determination of an endoscope pose within the anatomical region for an intra-operative visualization of an anatomical feature within the endoscope image, wherein the endoscope pose is derived from a delineation of a volume coordinate position of the anatomical feature within a pre-operative image of the anatomical region. The robotic control method further involves commanding the robot to move the endoscope to the endoscope pose within the anatomical region to visualize the anatomical feature within the endoscope image.

The term "pre-operative" as used herein is broadly defined to describe any activity executed before, during or after an endoscopic imaging of an anatomical region for purposes of acquiring a three-dimensional ("3D") image of the anatomical region. Examples of pre-operative imaging of the anatomical region includes, but are not limited to, computed tomography ("CT") imaging, magnetic resonance ("MR") imaging, X-ray imaging, and 3D ultrasound ("3D US") imaging before, during or after an endoscopic imaging of an anatomical region.

The term "intra-operative" as used herein is broadly defined to describe any activity executed by the robot unit and/or the control unit during an endoscopic imaging of the anatomical region. Examples of endoscopic imaging of the anatomical region include, but are not limited to, a coronary artery bypass grafting, a bronchoscopy, a colonscopy, a laparascopy, and a brain endoscopy.

Those having ordinary skill will appreciate the meaning of an "anatomical region" and an "anatomical feature" as known in the art. Nonetheless, examples of an anatomical region include, but are not limited to, head, neck, thorax, abdomen, back, pelvis and perineum. Also, examples of an anatomical feature include, but are not limited to, components and areas of an organ/organ system (e.g., blood vessels of a heart, a trachea of a respiratory system, a cerebellum of a brain, a fundus of a gallbladder, an area of a sigmoid colon).

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 1:
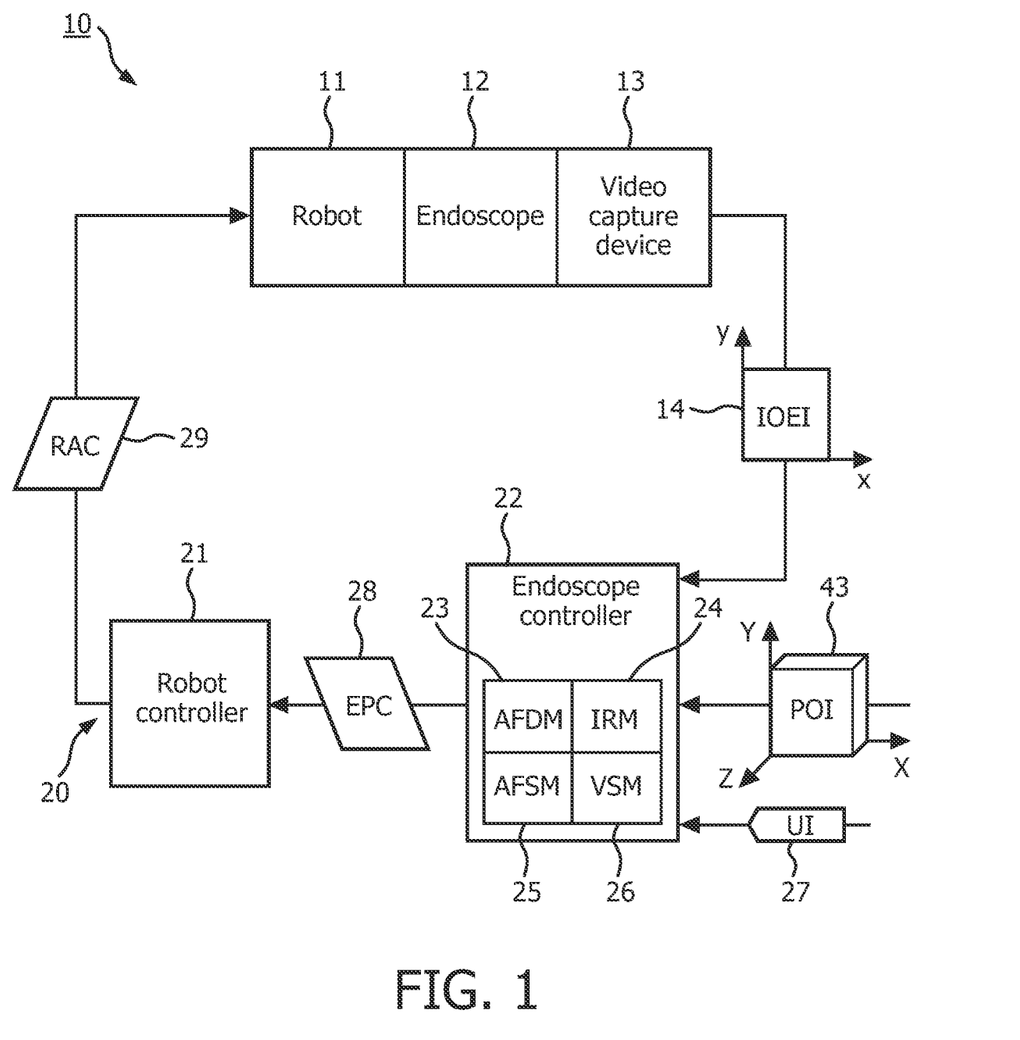
FIG. 1 illustrates an exemplary embodiment of a robotic control system in accordance with the present invention.

As shown in FIG. 1, a robotic guiding system employs a robot unit 10 and a control unit 20 for any endoscopic procedure involving an endoscopic imaging of one or more anatomical features of an anatomical region (e. Examples of such endoscopic procedures include, but are not limited to, minimally invasive cardiac surgery, minimally invasive diagnostic interventions (e.g., arthoscopy), laparoscopic surgery, natural orifice transluminal surgery, single incision laparoscopic surgery and pulmonary/bronchoscopic surgery.

In practice, the endoscopic imaging may be of any anatomical feature or section(s) therefore within any anatomical region. Nonetheless, to facilitate an understanding of the present invention, exemplary embodiments will be described in the context of an endoscopic imaging of a left anterior descending artery of a heart within a thorax region of a patient.

Robot unit 10 includes a robot 11, an endoscope 12 rigidly attached to robot 11 and a video capture device 13 attached to the endoscope 12.

Robot 11 is broadly defined herein as any robotic device structurally configured with motorized control of one or more joints for maneuvering an end-effector as desired for the particular endoscopic procedure. In practice, robot 11 may have four (4) degrees-of-freedom, such as, for example, a serial robot having joints serially connected with rigid segments, a parallel robot having joints and rigid segments mounted in parallel order (e.g., a Stewart platform known in the art) or any hybrid combination of serial and parallel kinematics.

Endoscope 12 is broadly defined herein as any device structurally configured with ability to image from inside a body. Examples of endoscope 12 for purposes of the present invention include, but are not limited to, any type of scope, flexible or rigid (e.g., endoscope, arthroscope, bronchoscope, choledochoscope, colonoscope, cystoscope, duodenoscope, gastroscope, hysteroscope, laparoscope, laryngoscope, neuroscope, otoscope, push enteroscope, rhinolaryngoscope, sigmoidoscope, sinuscope, thorascope, etc.) and any device similar to a scope that is equipped with an image system (e.g., a nested cannula with imaging). The imaging is local, and surface images may be obtained optically with fiber optics, lenses, and miniaturized (e.g. CCD based) imaging systems.

In practice, endoscope 12 is mounted to the end-effector of robot 11. A pose of the end-effector of robot 11 is a position and an orientation of the end-effector within a coordinate system of robot 11 actuators. With endoscope 12 mounted to the end-effector of robot 11, any given pose of the field-of-view of endoscope 12 (i.e., endoscope pose) within an anatomical region corresponds to a distinct pose of the end-effector of robot 11 within the robotic coordinate system. Consequently, each individual endoscope image of the anatomical region generated by endoscope 12 may be linked to a corresponding pose of the field-of-view of endoscope 12 within the robotic coordinate system.

Video capture device 13 is broadly defined herein as any device structurally configured with a capability to convert an endoscopic video signal from endoscope 12 into a computer readable temporal sequence of an endoscope image ("IOEI") 14. In practice, video capture device 13 may employ a frame grabber of any type for capturing individual digital still frames from the endoscopic video signal.

Still referring to FIG. 1, control unit 20 includes a robot controller 21 and an endoscope controller 22.

Robot controller 21 is broadly defined herein as any controller structurally configured to provide one or more robot actuator commands ("RAC") 29 to robot 11 for controlling a pose of the end-effector of robot 11 as desired for the endoscopic procedure. More particularly, robot controller 21 converts endoscope position commands ("EPC") 28 from endoscope controller 22 into robot actuator commands 29. For example, endoscope position commands 28 may indicate an endoscope path leading to desired three-dimensional position of a field-of-view of endoscope 12 within an anatomical region whereby robot controller 21 converts command 28 into commands 29 including an actuation current for each motor of robot 11 as needed to move endoscope 12 to the desired three-dimensional position of the field-of-view of endoscope 12 within an anatomical region.

Figure 2:
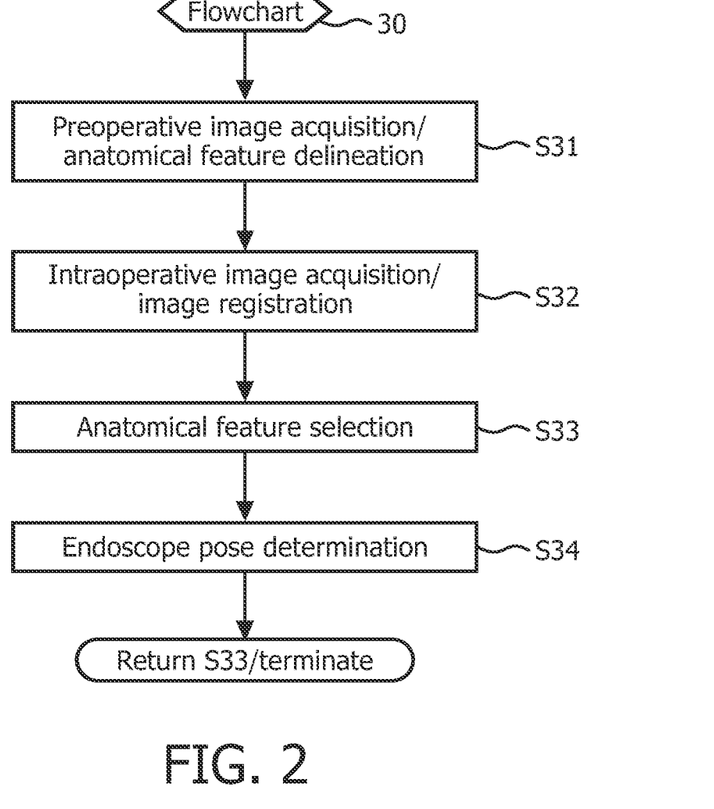
FIG. 2 illustrates a flowchart representative of an exemplary embodiment of a robotic control method in accordance with the present invention.

Endoscope controller 22 is broadly defined herein as any controller structurally configured for implementing a robotic control method in accordance with the present invention and exemplary shown in FIG. 2. To this end, endoscope controller 22 may incorporate anatomical feature delineation module ("AFDM") 23, an image registration module ("IRM") 24, anatomical feature selection module ("AFSM") 25 and a visual servo module ("VSM") 26.

Anatomical feature delineation module 23 is broadly defined herein as any module structurally configured for processing a user input ("UI") 27 to delineate a volume coordinate position (X, Y, Z) for each anatomical feature of interest thereof within a pre-operative image 43 of the anatomical region for an intra-operative visualization of the anatomical feature(s) within endoscope image 14. In particular, an anatomical feature delineation as exemplarily implemented by a stage S31 of flowchart 30 as shown in FIG. 2.

Image registration module 24 is broadly defined herein as any module structurally configured for registering pre-operative image 43 and endoscope image 14 as known in the art. In particular, an image registration as exemplarily implemented by a stage S32 of flowchart 30 shown in FIG. 2.

Anatomical feature selection module 25 is broadly defined herein as any module structurally configured for processing a user input 26 of a endoscopic viewing selection of a particular anatomical feature of interest or section(s). In particular, an anatomical feature selection exemplarily implemented by a stage S33 of flowchart 30 shown in FIG. 2.

Again, in context of FIG. 1, the term "visualize" as used herein is broadly defined to describe a robotic control of endoscope 12 within an anatomical region whereby an anatomical feature of interest or section(s) thereof is either visible, partially or entirely, within endoscope image 14 or obstructed from being visible within endoscope image 14 yet susceptible to a surgeon forming a mental picture of an outline of the anatomical feature or section(s) thereof, partially or entirely, within endoscope image 14.

Visual servo module 26 is broadly defined herein as any module structurally configured for determining and moving endoscope 12 to an endoscope pose within the anatomical region that facilitates a visualization of the selected anatomical feature(s) or section(s) thereof within endoscope image 14. In particular, an endoscope pose determination as exemplarily implemented by a stage S34 of flowchart 30 shown in FIG. 2.

A description of flowchart 30 will now be provided herein to facilitate a further understanding of endoscope controller 22.

Figure 3:
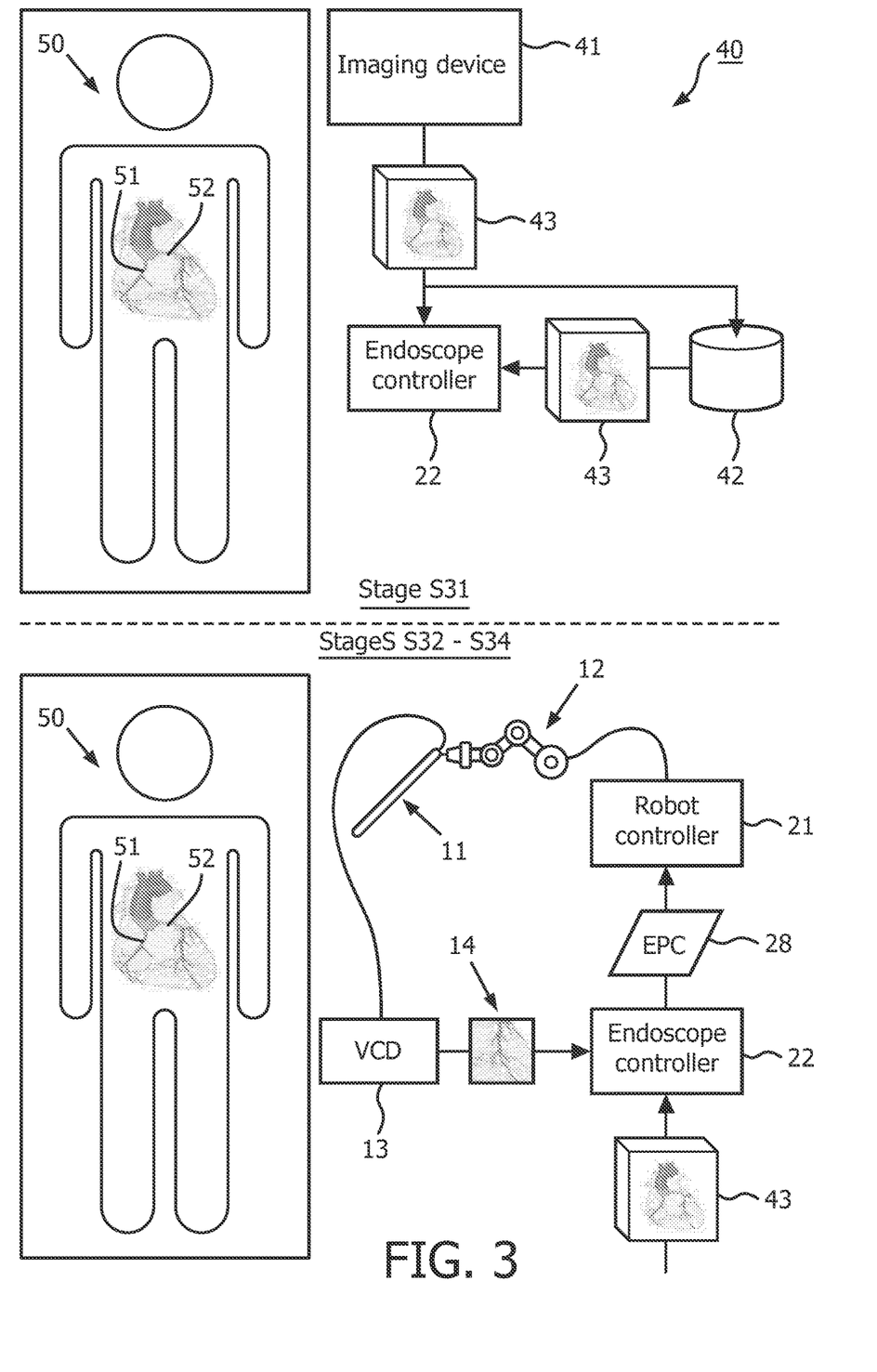
FIG. 3 illustrates an exemplary surgical implementation of the flowchart shown in FIG. 2.

Referring to FIG. 2, a stage S31 of flowchart 30 encompasses anatomical feature delineation module 23 acquiring pre-operative image 43. For example, as shown in FIG. 3, an imaging device 41 (e.g., a CT device, a MRI device, an X-ray device or a 3D US device) is operated to generate pre-operative image 43 of a thorax region of a patient 50 illustrating left and right coronary arteries 51 and 52 of patient 50. Anatomical feature delineation module 23 may acquire pre-operative image 43 as pre-operative image 43 is being generated by imaging device 41 as exemplarily shown in FIG. 3 or as previously stored in a database 42 as exemplarily shown in FIG. 3.

Anatomical feature delineation module 23 processes pre-operative image 43 to delineate a volume coordinate position for each anatomical feature of interest or section(s) thereof within the anatomical region. In practice, anatomical feature delineation module 23 may execute any technique for delineating the anatomical feature(s) of interest or section(s) thereof within pre-operative image 43. In one embodiment as shown in FIG. 4, anatomical feature delineation module 23 provides four (4) modes 23a-23d for delineating volume coordinate position(s) of anatomical feature(s) within pre-operative image 43.

Figure 4:
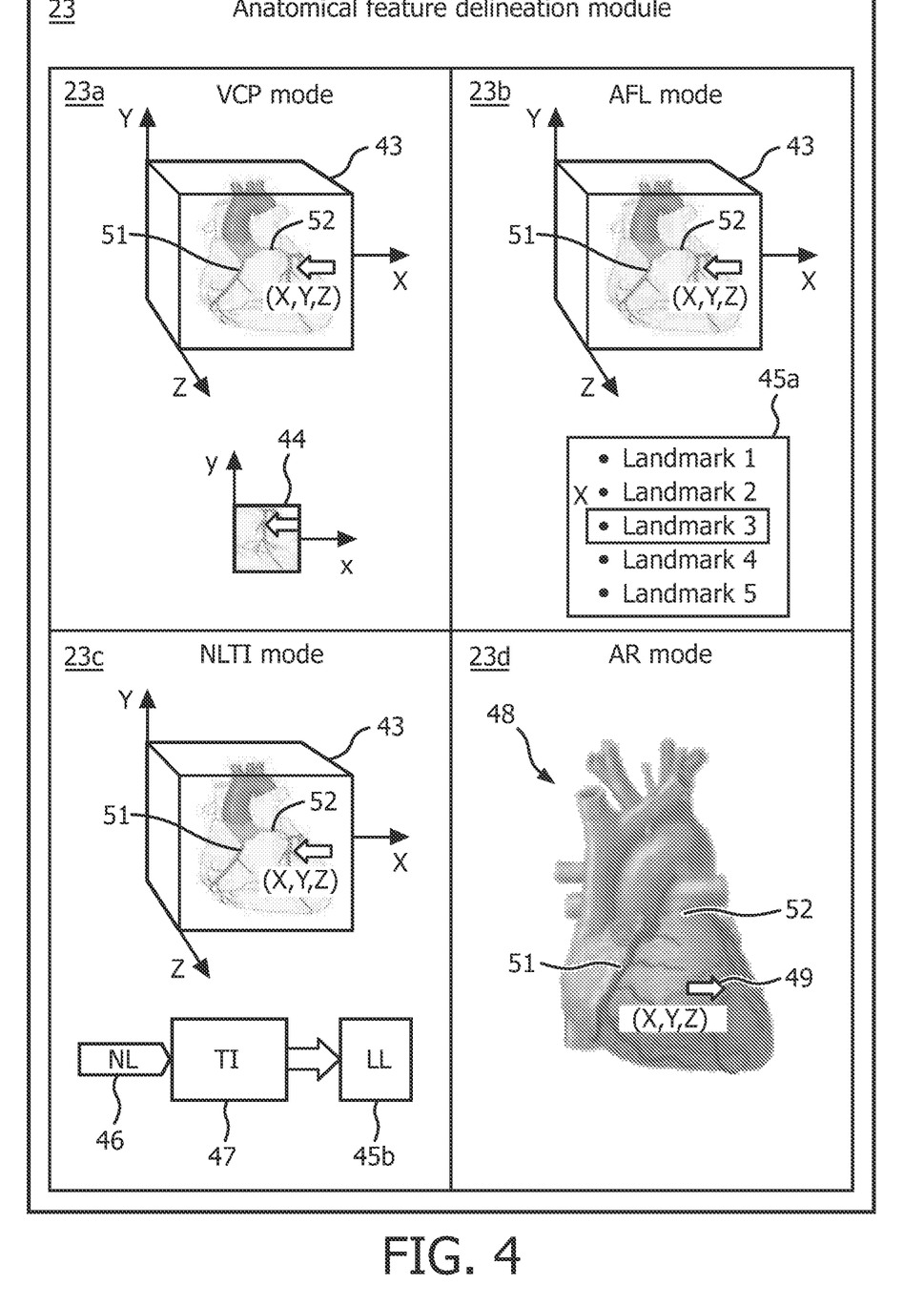
FIG. 4 illustrates an exemplary embodiment of an anatomical feature delineation module in accordance with the present invention.

Referring to FIG. 4, a volume coordinate position ("VCP") mode 23a delineates a volume coordinate position of each anatomical feature within pre-operative image 43 as selected by a user of module 23. Specifically, pre-operative image has a 3D coordinate system defined by an X-axis, a Y-axis and a Z-axis. A user may move a cursor arrow to an anatomical feature of interest or section(s) thereof within pre-operative image 43 or a two-dimensional view 44 of the cursor within preoperative image 43 defined by a x-axis and a y-axis. Upon a desired positioning of the cursor, the user may make a selection (e.g., a mouse click) of the anatomical feature or section(s) thereof facilitating a delineation of a volume coordinate position (X, Y, Z) of the anatomical feature. Additionally, the user may be able to rotate pre-operative image 43 and corresponding two-dimensional view 44 of the cursor within preoperative image 43 to orient the anatomical feature for desired view in the endoscope image. In this case, an orientation of the anatomical feature is delineated with the volume coordinate position (X, Y, Z). The cursor movement and user selection may be repeated as desired for other areas of the selected anatomical feature and/or for additional anatomical features.

Furthermore, a name may be assigned by the user to the selected anatomical feature(s) or section(s) thereof (e.g., "left anterior descending artery"). Particularly, when the user has interest in different sections of an anatomical feature (e.g., "upper section of left anterior descending artery", "middle section left anterior descending artery", and "lower section of left anterior descending artery").

An anatomical feature landmark ("AFL") mode 23b provides a pre-defined listing 45a of landmark names for each anatomical feature or section(s) thereof within pre-operative image 43 for VCP mode 23a. Any landmark selected in listing 45a (e.g., left anterior descending artery as landmark 3) is highlighted within pre-operative image 43 via a cursor arrow. The user may move the cursor arrow relative to the highlighted anatomical feature to select section(s) of interest of the anatomical feature. Upon a desired positioning of the cursor, the user may make a selection (e.g., a mouse click) of the anatomical feature facilitating a delineation of a volume coordinate position (X, Y, Z) and optional orientation of the anatomical feature or section thereof as described by VCP mode 23a and to name the anatomical feature, particularly selected section(s).

A natural language interpretation mode ("NTLI") 23c utilizes a text interpreter ("TI") 47 to interpret natural language to generates a landmark listing 45b for VCP 23a. Specifically, text interpreter 47 is used to interpret and convert free-text instructions generated during surgical planning to anatomical features which are then stored to be used to move endoscope 12 during the delineation process and/or endoscopic surgery. Anatomical descriptions are extracted into codes in a well-defined medical ontology (e.g., Systematized Nomenclature of Medicine ("SNOMED") or the Foundational Model of Anatomy ("FMA").

The following is an example of a free text report: "EKG showed nonspecific ST segment changes. Echocardiography showed a normal left ventricle with some mild hypertrophy. On diagnostic cardiac catheterization, a lesion to the left anterior descending artery was identified. There was about 80% stenosis in the circumflex system. The posterior descending artery had about a 70% stenosis. Bypass surgery recommended" From this report, text interpreter 47 extracts anatomical features: left anterior descending artery, circumflex system, posterior descending artery, etc. Further, from the ontology, the text interpreter 47 may determine anatomical relationship between identified anatomy (e.g., left descending artery and left circumflex artery arise from the left main artery). Further, general location markers, such as "posterior" may be extracted and associated with a specific landmark. Thereafter, landmark listing 45b may be used in the same manner as landmark listing 45a to highlight anatomical features within pre-operative image 43 of the anatomical region for VCP mode 23a.

Atlas registration ("AR") mode 23d involves a registration of an atlas of the anatomical region to pre-operative image 43 whereby each anatomical feature of the atlas are associated with a corresponding anatomical feature within the pre-operative image. Consequently, a user may utilize the atlas of the anatomical region to select and delineate anatomical features of interest or section(s) thereof analogous to VCP mode 23a. For example, a registration of atlas 48 of the thorax region (shown as a picture of the heart in FIG. 4) to pre-operative image 43 enables anatomical features of atlas 48 to be associated with corresponding anatomical features within pre-operative image 43 (e.g. left anterior descending artery 49 of atlas 48). Thus, a selection of an anatomical feature or section thereof of atlas 48 delineates a volume coordinate position and an optional orientation within pre-operative image 43.

Referring back to FIG. 2, a stage S32 of flowchart 30 encompasses image registration module 24 acquiring and registering endoscope image 14 with pre-operative image 43 as known in the art. In one embodiment, module 24 may implement a point based registration of endoscope image 14 with pre-operative image 43. In another embodiment, module 24 may implement a graphical matching registration of endoscope image 14 with pre-operative image 43 involving a matching of graphical representations of anatomical features (e.g., blood vessel trees) in endoscope image 14 and pre-operative image 43.

Upon completion of stage S32, a stage S33 of flowchart 30 encompasses anatomical feature selection module 25 receiving a user input to VSM 26 (FIG. 1) of an anatomical feature of interest or section thereof to facilitate a subsequent determination of an endoscope pose of endoscope 12 within the anatomical region for visualizing the anatomical feature or section thereof within endoscope image 14. In practice, module 25 may provide one or more views of the anatomical region in dependence of the mode (FIG. 4) used to delineate the volume coordinate position and optional orientation of the anatomical features. For example, marked or named anatomical features or section(s) thereof may be shown in an image of the anatomical region or a designed computer screen whereby the user may interact with image or the screen to select the anatomical feature or section thereof (e.g., a keyboard, a mouse, a touchscreen, a voice command, a gesture, etc.). Also by example, the registered atlas may be presented whereby the user may interact with the atlas to select the anatomical feature or section thereof. By further example, a listing of landmark names may be presented to facilitate a selection of an anatomical feature or section thereof.

Still referring to FIG. 2, a stage S34 of flowchart 30 encompasses visual servo module 26 determining an endoscope pose of endoscope 12 within the anatomical region for visualizing the selected anatomical feature or section thereof within endoscope image 14, and generating endoscope position commands 28 to robot controller 21 to thereby guide endoscope 12 (FIG. 1) to the determined endoscope pose.

Specifically, from the image registration of stage S32 and the anatomical feature selection of stage S33, the delineated volume coordinate position (X, Y, Z) within pre-operative image 43 corresponds to a frame coordinate position (x, y) within endoscope image 14 that provides for a visualization of the anatomical feature at volume coordinate position (X, Y, Z) (e.g., a center frame coordinate position of endoscope image 14) of pre-operative image 43. Additionally, the frame coordinate position (x, y) may be oriented in accordance with a delineated endoscopic view orientation.

If endoscope 12 is calibrated (i.e., the endoscope camera parameters like focal length and optical center of endoscope image 14 are known), then a relationship between frame coordinate position (x, y) within endoscope image 14 and a pose of endoscope 12 within the anatomical region may be established as known in the art. Assuming further that the spatial transformation between endoscope 12 and joints of robot 11 is known from robot calibration procedures known in art, the relationship between the robot joints and image space may be derived. This relationship is referred to, in art, as Image Jacobian. From the Image Jacobian, robot joint values may be computed whereby, after robot 11 has moved endoscope 12 to the computed volume coordinate position (X, Y, Z), the anatomical feature is located at the desired frame coordinate position (x, y) of endoscope image 14 (e.g., a center of the image).

Figure 5:
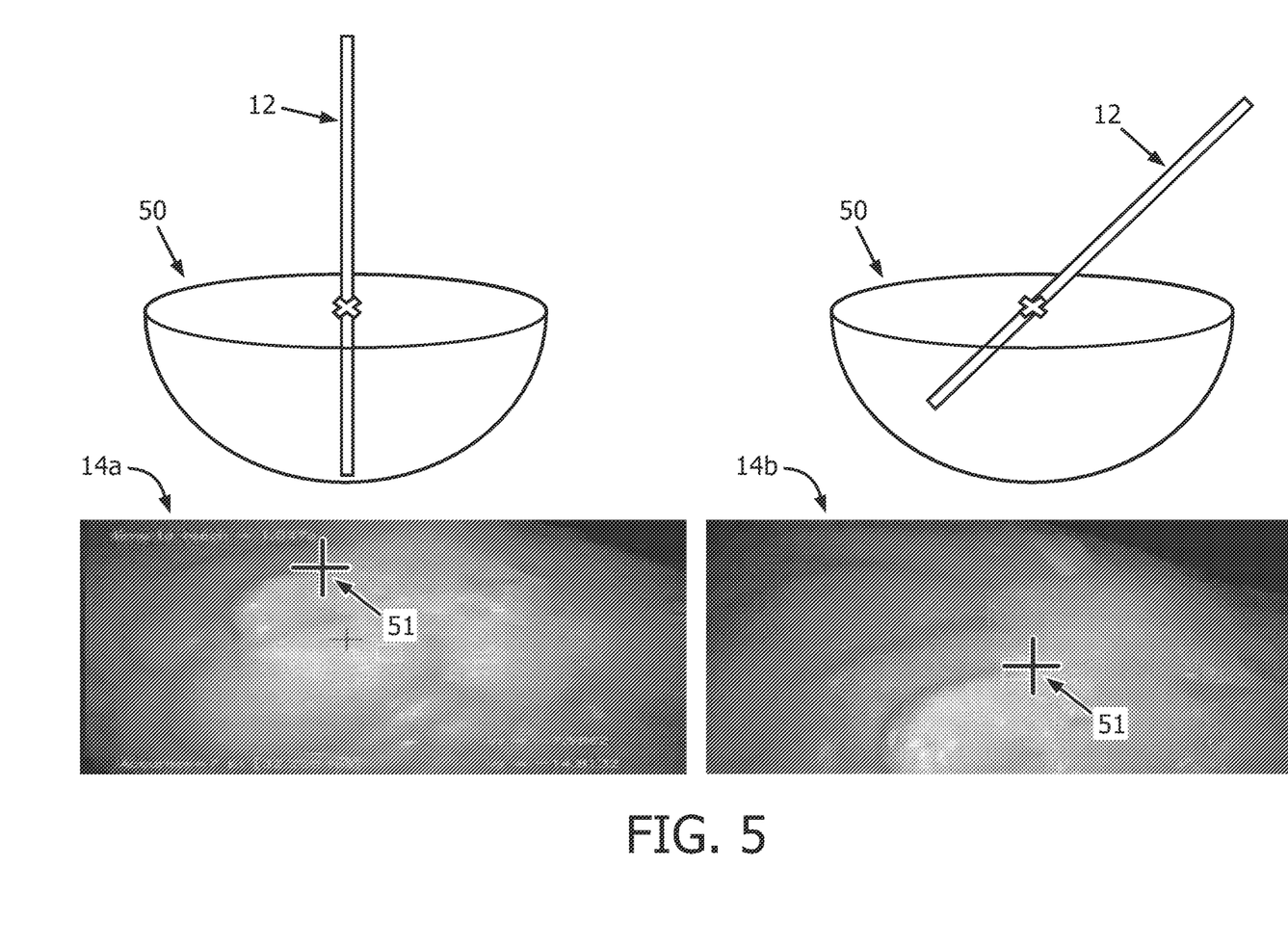
FIGS. 5 and 6 illustrate exemplary implementations of an endoscope movement in accordance with the flowchart shown in FIG. 2.

If endoscope 12 is not calibrated and/or the transformation between the endoscope 12 and joints of robot 11 is not known, then uncalibrated visual servoing of robot 11 as known in the art may be utilized to determine and move endoscope 12 to a pose within the anatomical region to visualize the anatomical feature or section thereof in accordance with the frame coordinate position (x, y) within endoscope image 14 (e.g., an uncalibrated velocity optimization method For example, referring to FIG. 5, an anatomical feature 51 within an endoscope image 14a is covered by fat and obstructed from view. Nonetheless, once a surgeon picks the anatomical feature, endoscope 12 may be moved on a semi-sphere (touching the sphere) so that anatomical feature 51 goes in the middle of an endoscope image 14b. Note that endoscope 12 is pivoted around a fixed point based on distance between anatomical feature 51 as shown in images 14a and 14b.

Figure 6:
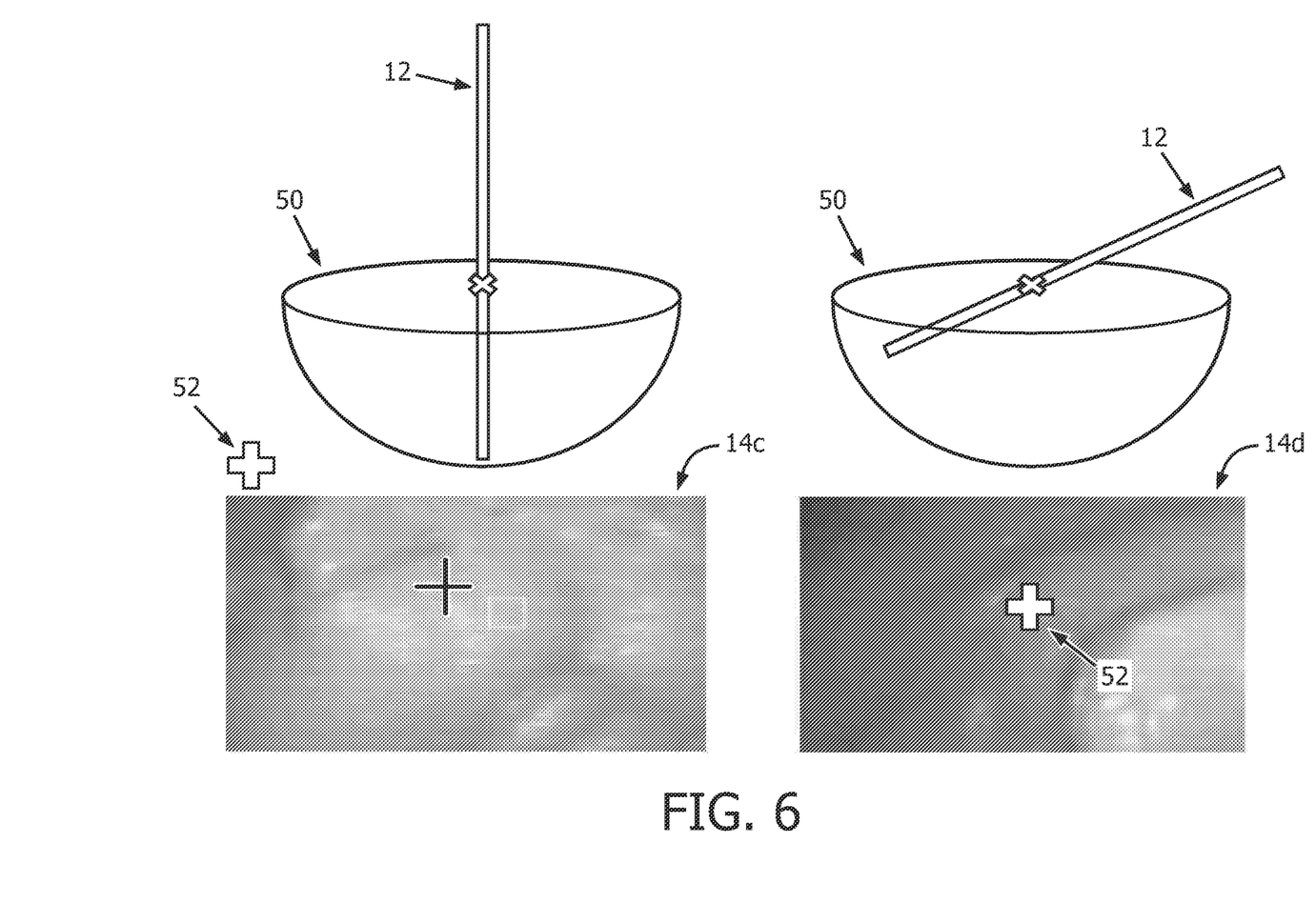

By further example, referring to FIG. 6, a selected anatomical feature 52 is outside the view of endoscope image 14c. Endoscope 12 may be moved again on a sphere 50 to anatomical feature 52 in the middle of endoscope image 14d. More particularly, an analogous distance between points within endoscope image 14c may serve to ascertain correction motion parameters for uncalibrated visual servoing of robot 11.

Referring back to FIG. 2, stages S33 and S34 may be executed in a loop until such time robot 11 has moved endoscope 12 to each desired pose within the anatomical region.

In practice, modules 23-26 (FIG. 1) may be implemented by hardware, software and/or firmware integrated within endoscope controller 22 as shown.

Robot controller 21 and endoscope controller 22 may be physically separate controllers or logically controllers integrated within a single physical controller.

From the description of FIGS. 1-6 herein, those having ordinary skill in the art will appreciate the numerous benefits of the present invention including, but not limited to, an application of the present invention to any type of endoscopy surgery involving a visualization of a particular anatomical feature or section thereof within an anatomical region.

Although the present invention has been described with reference to exemplary aspects, features and implementations, the disclosed systems and methods are not limited to such exemplary aspects, features and/or implementations. Rather, as will be readily apparent to persons skilled in the art from the description provided herein, the disclosed systems and methods are susceptible to modifications, alterations and enhancements without departing from the spirit or scope of the present invention. Accordingly, the present invention expressly encompasses such modification, alterations and enhancements within the scope hereof.

The invention claimed is:

1. A robotic control system, comprising:
   a robot unit, comprising:
   an endoscope configured to generate an endoscope image, and
   a robot configured to move the endoscope within an anatomical region; and
   a control unit, comprising:
   an endoscope controller configured to determine an endoscope pose within the anatomical region for an intra-operative visualization of an anatomical feature within the endoscope image, wherein the endoscope controller is configured to pre-operatively delineate a volume coordinate position of the anatomical feature within a pre-operative image of the anatomical region, wherein the volume coordinate position is a three-dimensional volume coordinate position based on a 3D coordinate system of the pre-operative image, and wherein the determined endoscope pose is derived by the endoscope controller from an intra-operative selection of a pre-operative description of the anatomical feature for the intra-operative visualization of the anatomical feature within the endoscope image based on a registration of the pre-operative image with the endoscope image, wherein the pre-operative description of the anatomical feature corresponds to the pre-operative delineation of the volume coordinate position of the anatomical feature within the pre-operative image of the anatomical region, and a robot controller configured to command the robot to move the endoscope to the endoscope pose within the anatomical region to for the intra-operative visualization of the anatomical feature within the endoscope image, wherein the endoscope controller is configured to pre-operatively delineate the volume coordinate position of the anatomical feature within the pre-operative image of the anatomical region by pre-operatively providing to a user:

a pre-defined listing of landmark names of landmarks of the anatomical region for selection of a landmark name of the pre-defined listing of landmark names to facilitate the pre-operative delineation of the volume coordinate position of the anatomical feature within the pre-operative image of the anatomical region based on the selected landmark name;

an atlas of the anatomical region registered to the pre-operative image for selection of an anatomical feature of the atlas to facilitate the pre-operative delineation of the volume coordinate position of the anatomical feature within the pre-operative image of the anatomical region based on the selected anatomical feature of the atlas, wherein each anatomical feature of the atlas is associated with a corresponding anatomical feature within the pre-operative image; or both the pre-defined listing of landmark names of landmarks of the anatomical region and the atlas of the anatomical region registered to the pre-operative image.

2. The robotic control system of claim 1, wherein the endoscope controller is further configured to provide to the user the volume coordinate position of the anatomical feature within the pre-operative image of the anatomical region as the pre-operative description of the anatomical feature to facilitate the intra-operative selection of the pre-operative description for visualization of the anatomical feature within the endoscope image.

3. The robotic control system of claim 1, wherein the pre-operative description of the anatomical feature comprises a landmark name, a code of the anatomical feature, or both the landmark name and the code of the anatomical feature.

4. The robotic control system of claim 1, wherein the configuration of the endoscope controller to provide to the user the atlas of the anatomical region registered to the pre-operative image also facilitates correspondence of the pre-operative description of the anatomical feature with the pre-operative delineation of the volume coordinate position of the anatomical feature within the pre-operative image of the anatomical region.

5. The robotic control system of claim 1, wherein the endoscope pose is further derived by the endoscope controller from a pre-operative delineation of a position and an orientation of an end-effector of the endoscope associated with a two-dimensional view of the anatomical feature within the pre-operative image of the anatomical region.

6. The robotic control system of claim 1, wherein the configuration of the endoscope controller to provide the pre-defined listing of landmark names of landmarks of the anatomical region also facilitates correspondence of the pre-operative description of the anatomical feature with the pre-operative delineation of the volume coordinate position of the anatomical feature within the pre-operative image of the anatomical region.

7. The robotic control system of claim 1, wherein the endoscope controller is further configured to:

interpret natural language surgical instructions to facilitate correspondence of the pre-operative description of the anatomical feature with the pre-operative delineation of the volume coordinate position of the anatomical feature within the pre-operative image of the anatomical region; and construct a listing of landmark names of landmarks of the anatomical region based on interpreted natural language surgical instructions.

8. The robotic control system of claim 1, wherein the volume coordinate position is a three-dimensional volume coordinate position (X, Y, Z), and wherein the endoscope controller is further configured to translate the three-dimensional volume coordinate position of the anatomical feature within the pre-operative image to a two-dimensional frame coordinate position (x, y) of the anatomical feature within the endoscope image.

9. The robotic control system of claim 1, wherein the endoscope controller is configured to generate endoscope position commands, in response to the determined endoscope pose, for guiding the endoscope to the determined endoscope pose based on the pre-operative delineation of the volume coordinate position of the anatomical feature within the pre-operative image of the anatomical region, and to supply the endoscope position commands to the robot controller to drive the endoscope to the determined endoscope pose, and wherein the robot controller is configured to command the robot to move the endoscope to the determined endoscope pose within the anatomical region for the intra-operative visualization of the anatomical feature within the endoscope image in response to the endoscope position commands received from the endoscope controller.

10. The robotic control system of claim 9, wherein the endoscope controller receives an endoscopic video signal from the endoscope and is configured to execute visual servoing in response to the endoscopic video signal received from the endoscope to drive the endoscope to the determined endoscope pose.

11. The robotic control system of claim 1, wherein the anatomical feature is at least partially obstructed from being visible during the intra-operative visualization.

12. The robotic control system of claim 1, wherein the endoscope controller is configured to pre-operatively provide to the user the atlas of the anatomical region registered to the pre-operative image for selection of the anatomical feature of the atlas to facilitate the pre-operative delineation of the volume coordinate position of the anatomical feature within the pre-operative image of the anatomical region based on the selected anatomical feature of the atlas, wherein each anatomical feature of the atlas is associated with a corresponding anatomical feature within the pre-operative image.

13. A control unit for an endoscope configured to generate an endoscope image with a robot configured to move the endoscope within an anatomical region, the control unit comprising:

an endoscope controller configured to determine an endoscope pose within the anatomical region for an intra-operative visualization of an anatomical feature within the endoscope image, wherein the endoscope controller is configured to pre-operatively delineate a volume coordinate position of the anatomical feature within a pre-operative image of the anatomical region, wherein the volume coordinate position is a three-dimensional volume coordinate position based on a 3D coordinate system of the pre-operative image, and wherein the determined endoscope pose is derived by the endoscope controller from an intra-operative selection of a pre-operative description of the anatomical feature for the intra-operative visualization of the anatomical feature within the endoscope image based on a registration of the pre-operative image with the endoscope image, wherein the pre-operative description of the anatomical feature corresponds to the pre-operative delineation of the volume coordinate position of the anatomical feature within the pre-operative image of the anatomical region; and a robot controller configured to command the robot to move the endoscope to the endoscope pose within the anatomical region for the intra-operative visualization of the anatomical feature within the endoscope image, wherein the endoscope controller is configured to pre-operatively delineate the volume coordinate position of the anatomical feature within the pre-operative image of the anatomical region by pre-operatively providing to a user:

a pre-defined listing of landmark names of landmarks of the anatomical region for selection of a landmark name of the pre-defined listing of landmark names to facilitate the pre-operative delineation of the volume coordinate position of the anatomical feature within the pre-operative image of the anatomical region based on the selected landmark name;

an atlas of the anatomical region registered to the pre-operative image for selection of an anatomical feature of the atlas to facilitate the pre-operative delineation of the volume coordinate position of the anatomical feature within the pre-operative image of the anatomical region based on the selected anatomical feature of the atlas, wherein each anatomical feature of the atlas is associated with a corresponding anatomical feature within the pre-operative image; or both the pre-defined listing of landmark names of landmarks of the anatomical region and the atlas of the anatomical region registered to the pre-operative image.

14. The control unit of claim 13, wherein the endoscope controller is further configured to provide to the user the volume coordinate position of the anatomical feature within the pre-operative image of the anatomical region as the pre-operative description of the anatomical feature to facilitate the intra-operative selection of the pre-operative description for visualization of the anatomical feature within the endoscope image.

15. The control unit of claim 13, wherein the configuration of the endoscope controller to provide to the user the atlas of the anatomical region registered to the pre-operative image also facilitates correspondence of the pre-operative description of the anatomical feature with the pre-operative delineation of the volume coordinate position of the anatomical feature within the pre-operative image of the anatomical region.

16. The control unit of claim 13, wherein the endoscope pose is further derived by the endoscope controller from a pre-operative delineation of a position and an orientation of an end-effector of the endoscope associated with a two-dimensional view of the anatomical feature within the pre-operative image of the anatomical region.

17. The control unit of claim 13, wherein the configuration of the endoscope controller to provide the pre-defined listing of landmark names of landmarks of the anatomical region also facilitates correspondence of the pre-operative description of the anatomical feature with the pre-operative delineation of the volume coordinate position of the anatomical feature within the pre-operative image of the anatomical region.

18. The control unit of claim 13, wherein the endoscope controller is further configured to:

interpret natural language surgical instructions to facilitate correspondence of the pre-operative description of the anatomical feature with the pre-operative delineation of the volume coordinate position of the anatomical feature within the pre-operative image of the anatomical region; and construct a listing of landmark names of landmarks of the anatomical region based on interpreted natural language surgical instructions.

19. The control unit of claim 13, wherein the volume coordinate position is a three-dimensional volume coordinate position (X, Y, Z), and wherein the endoscope controller is further configured to translate the three-dimensional volume coordinate position of the anatomical feature within the pre-operative image to a two-dimensional frame coordinate position (x, y) of the anatomical feature within the endoscope image.

20. The control unit of claim 13, wherein the endoscope controller is configured to generate endoscope position commands, in response to the determined endoscope pose, for guiding the endoscope to the determined endoscope pose based on the pre-operative delineation of the volume coordinate position of the anatomical feature within the pre-operative image of the anatomical region, and to supply the endoscope position commands to the robot controller to drive the endoscope to the determined endoscope pose, and wherein the robot controller is configured to command the robot to move the endoscope to the determined endoscope pose within the anatomical region for the intra-operative visualization of the anatomical feature within the endoscope image in response to the endoscope position commands received from the endoscope controller.

21. The control unit of claim 20, wherein the endoscope controller receives an endoscopic video signal from the endoscope and is configured to execute visual servoing in response to the endoscopic video signal received from the endoscope to drive the endoscope to the determined endoscope pose.

22. The control unit of claim 13, wherein the anatomical feature is at least partially obstructed from being visible during the intra-operative visualization.

23. The control unit of claim 13, wherein the endoscope controller is configured to pre-operatively provide to the user the atlas of the anatomical region registered to the pre-operative image for selection of the anatomical feature of the atlas to facilitate the pre-operative delineation of the volume coordinate position of the anatomical feature within the pre-operative image of the anatomical region based on the selected anatomical feature of the atlas, wherein each anatomical feature of the atlas is associated with a corresponding anatomical feature within the pre-operative image.

\* \* \* \* \*